(12) United States Patent
Greally et al.

(10) Patent No.: US 8,642,294 B2
(45) Date of Patent: Feb. 4, 2014

(54) METHODS FOR DETERMINING CYTOSINE METHYLATION IN DNA AND USES THEREOF

(75) Inventors: John M. Greally, New York, NY (US); Eli Hatchwell, St. James, NY (US)

(73) Assignees: Albert Einstein College of Medicine of Yeshiva University, Bronx, NY (US); The Research Foundation State University of New York, Albany, NY (US)

( * ) Notice: Subject to any disclaimer, the term of this patent is extended or adjusted under 35 U.S.C. 154(b) by 303 days.

(21) Appl. No.: 12/451,431

(22) PCT Filed: May 19, 2008

(86) PCT No.: PCT/US2008/006387
§ 371 (c)(1),
(2), (4) Date: Mar. 16, 2010

(87) PCT Pub. No.: WO2008/156536
PCT Pub. Date: Dec. 24, 2008

(65) Prior Publication Data
US 2010/0267021 A1      Oct. 21, 2010

Related U.S. Application Data

(60) Provisional application No. 60/936,691, filed on Jun. 20, 2007.

(51) Int. Cl.
*C12P 19/34* (2006.01)
(52) U.S. Cl.
USPC ..................... 435/91.2; 435/91.52

(58) Field of Classification Search
None
See application file for complete search history.

(56) References Cited

U.S. PATENT DOCUMENTS

| | | | |
|---|---|---|---|
| 6,300,071 B1 | 10/2001 | Vuylsteke et al. | |
| 6,677,121 B2* | 1/2004 | Latimer et al. | 435/6.12 |
| 6,958,225 B2* | 10/2005 | Dong | 435/91.2 |
| 7,132,240 B2 | 11/2006 | Luo et al. | |
| 2003/0049663 A1 | 3/2003 | Wigler et al. | |
| 2003/0165952 A1* | 9/2003 | Linnarsson et al. | 435/6 |
| 2004/0072217 A1* | 4/2004 | Kennedy | 435/6 |
| 2005/0272065 A1* | 12/2005 | Lakey et al. | 435/6 |
| 2007/0259351 A1 | 11/2007 | Chinitz et al. | |
| 2008/0064030 A1* | 3/2008 | Petronis et al. | 435/6 |

OTHER PUBLICATIONS

Kaiser et al. (2002) Clinical Biochemistry vol. 35 pp. 49-52.*
Henke et al. (1997) Nucleic acids research vol. 25 No. 19 pp. 3957-3958.*
Khulan et al. (2006) vol. 16:1046-1055 (published online Jun. 29, 2006).*
PCT Notification of Transmittal of The International Search Report and The Written Opinion of the International Searching Authority, or the Declaration dated Aug. 8, 2008 by the U.S. Patent Office in connection with PCT International Patent Application No. PCT/US2008/006387, 10 pages.

(Continued)

*Primary Examiner* — Suchira Pande
(74) *Attorney, Agent, or Firm* — Amster, Rothstein & Ebenstein LLP

(57) ABSTRACT

Methods are described for determining the pattern of cytosine methylation in a DNA specimen, where the methods involve comparing the amount of DNA fragments generated by a methylation-sensitive restriction enzyme with the amount of DNA fragments generated by a methylation-insensitive isoschizomer of the methylation-sensitive restriction enzyme.

31 Claims, 4 Drawing Sheets

(56) References Cited

OTHER PUBLICATIONS

Ikegami K et al., entitled "Genome-wide and locus-specific DNA hypomethylation in G9a deficient mouse embryonic stem cells," Genes to Cells (2007) 12, 1-11.

Khulan B et al., entitled "Comparative isoschizomer profiling of cytosine methylation: The HELP assay," Genome Research, 16:1046-1055, 2006. Epub Jun. 29, 2006.

Lieb J D et al., entitled "Applying Whole-Genome Studies of Epigenetic Regulation to Study Human Disease," Cytogenet Genome Res. 2006; 114(1):1-15.

Siebert P D et al., entitled "An improved PCR method for walking in uncloned genomic DNA," Nucleic Acids Research, 1995, vol. 23, No. 6, 1087-1088.

Zhu J et al., entitled "Use of DNA Methylation for Cancer Detection and Molecular Classification," Journal of Biochemistry and Molecular Biology, vol. 40, No. 2, Mar. 2007, 135-141.

PCT Notification Concerning Transmittal of International Preliminary Report on Patentability and Written Opinion of the International Searching Authority dated Dec. 22, 2009 in connection with PCT International Patent Application No. PCT/US2008/006387, 6 pages.

\* cited by examiner

SEQUENCE LISTING

```
<160> NUMBER OF SEQ ID NOS: 34

<210> SEQ ID NO 1
<211> LENGTH: 12
<212> TYPE: DNA
<213> ORGANISM: Artificial
<220> FEATURE:
<223> OTHER INFORMATION: primer

<400> SEQUENCE: 1
cggctgttca tg                                                         12

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
cgacgtcgac tatccatgaa cagc                                            24

<210> SEQ ID NO 3
<211> LENGTH: 12
<212> TYPE: DNA
<213> ORGANISM: Artificial
<220> FEATURE:
<223> OTHER INFORMATION: Primer

<400> SEQUENCE: 3
cggcttccct cg                                                         12

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4
gcaactgtgc tatccgaggg aagc                                            24

<210> SEQ ID NO 5
<211> LENGTH: 4
<212> TYPE: DNA
<213> ORGANISM: Artificial
<220> FEATURE:
<223> OTHER INFORMATION: Recognition Site

<400> SEQUENCE: 5 ccgg                                                                   4
```

```
<210> SEQ ID NO 6
<211> LENGTH: 6
<212> TYPE: DNA
<213> ORGANISM: Artificial
<220> FEATURE:
<223> OTHER INFORMATION: Recognition Site

<400> SEQUENCE: 6 accggt                                                                         6

<210> SEQ ID NO 7
<211> LENGTH: 9
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (5)..(5)
<223> OTHER INFORMATION: n = a, c, g, or t

<400> SEQUENCE: 7 cacgncgtc                                                                      9

<210> SEQ ID NO 8
<211> LENGTH: 6
<212> TYPE: DNA
<213> ORGANISM: Artificial
<220> FEATURE:
<223> OTHER INFORMATION: Recognition Site

<400> SEQUENCE: 8 cccggg                                                                         6

<210> SEQ ID NO 9
<211> LENGTH: 6
<212> TYPE: DNA
<213> ORGANISM: Artificial
<220> FEATURE:
<223> OTHER INFORMATION: Recognition Site

<400> SEQUENCE: 9 ccgctc                                                                         6

<210> SEQ ID NO 10
<211> LENGTH: 6
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (2)..(2)
<223> OTHER INFORMATION: Y = C or T

<400> SEQUENCE: 10 cycgrg                                                                         6

<210> SEQ ID NO 11
<211> LENGTH: 9
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(6)
<223> OTHER INFORMATION: n = a, c, g or t
```

```
<400> SEQUENCE: 11 gannnnttc                                                                9

<210> SEQ ID NO 12
<211> LENGTH: 6
<212> TYPE: DNA
<213> ORGANISM: Artificial
<220> FEATURE:
<223> OTHER INFORMATION: Recognition Site

<400> SEQUENCE: 12 gacgtc                                                                   6

<210> SEQ ID NO 13
<211> LENGTH: 6
<212> TYPE: DNA
<213> ORGANISM: Artificial
<220> FEATURE:
<223> OTHER INFORMATION: Recognition Site

<400> SEQUENCE: 13 gagctc                                                                   6

<210> SEQ ID NO 14
<211> LENGTH: 5
<212> TYPE: DNA
<213> ORGANISM: Artificial
<220> FEATURE:
<223> OTHER INFORMATION: Recognition Site

<400> SEQUENCE: 14 gagtc                                                                    5

<210> SEQ ID NO 15
<211> LENGTH: 4
<212> TYPE: DNA
<213> ORGANISM: Artificial
<220> FEATURE:
<223> OTHER INFORMATION: Recognition Site

<400> SEQUENCE: 15 gatc                                                                     4

<210> SEQ ID NO 16
<211> LENGTH: 5
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(3)
<223> OTHER INFORMATION: W = A or T

<400> SEQUENCE: 16 gawtc                                                                    5

<210> SEQ ID NO 17
<211> LENGTH: 5
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(3)
<223> OTHER INFORMATION: n = a, c, g or t
```

```
<400> SEQUENCE: 17 gcngc                                                                  5

<210> SEQ ID NO 18
<211> LENGTH: 5
<212> TYPE: DNA
<213> ORGANISM: Artificial
<220> FEATURE:
<223> OTHER INFORMATION: Recognition Site

<400> SEQUENCE: 18 gcggc                                                                  5

<210> SEQ ID NO 19
<211> LENGTH: 11
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(9)
<223> OTHER INFORMATION: n = a, c, g, or t

<400> SEQUENCE: 19
gcnnnnnnng c                                                          11

<210> SEQ ID NO 20
<211> LENGTH: 6
<212> TYPE: DNA
<213> ORGANISM: Artificial
<220> FEATURE:
<223> OTHER INFORMATION: Recognition Site

<400> SEQUENCE: 20 gctagc                                                                 6

<210> SEQ ID NO 21
<211> LENGTH: 4
<212> TYPE: DNA
<213> ORGANISM: Artificial
<220> FEATURE:
<223> OTHER INFORMATION: Recognition Site

<400> SEQUENCE: 21 ggcc                                                                   4

<210> SEQ ID NO 22
<211> LENGTH: 6
<212> TYPE: DNA
<213> ORGANISM: Artificial
<220> FEATURE:
<223> OTHER INFORMATION: Recognition Site

<400> SEQUENCE: 22 ggcgcc                                                                 6

<210> SEQ ID NO 23
<211> LENGTH: 5
<212> TYPE: DNA
<213> ORGANISM: Artificial
<220> FEATURE:
<223> OTHER INFORMATION: Recognition Site

<400> SEQUENCE: 23 gtccc                                                                  5
```

```
<210> SEQ ID NO 24
<211> LENGTH: 6
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(4)
<223> OTHER INFORMATION: n = a, c, g, or t

<400> SEQUENCE: 24 ggnncc                                                                   6

<210> SEQ ID NO 25
<211> LENGTH: 6
<212> TYPE: DNA
<213> ORGANISM: Artificial
<220> FEATURE:
<223> OTHER INFORMATION: Recognition Site

<400> SEQUENCE: 25 ggtacc                                                                   6

<210> SEQ ID NO 26
<211> LENGTH: 5
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (3)..(3)
<223> OTHER INFORMATION: W = A or T

<400> SEQUENCE: 26 ggwcc                                                                    5

<210> SEQ ID NO 27
<211> LENGTH: 6
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (2)..(2)
<223> OTHER INFORMATION: R = G or A

<400> SEQUENCE: 27 grcgyc                                                                   6

<210> SEQ ID NO 28
<211> LENGTH: 4
<212> TYPE: DNA
<213> ORGANISM: Artificial
<220> FEATURE:
<223> OTHER INFORMATION: Recognition Site

<400> SEQUENCE: 28 gtac                                                                     4

<210> SEQ ID NO 29
<211> LENGTH: 5
<212> TYPE: DNA
<213> ORGANISM: Artificial
<220> FEATURE:
<223> OTHER INFORMATION: Recognition Site
```

-continued

```
<400> SEQUENCE: 29 gtctc                                                                     5

<210> SEQ ID NO 30
<211> LENGTH: 5
<212> TYPE: DNA
<213> ORGANISM: Artificial
<220> FEATURE:
<223> OTHER INFORMATION: Recognition Site

<400> SEQUENCE: 30 gagac                                                                     5

<210> SEQ ID NO 31
<211> LENGTH: 8
<212> TYPE: DNA
<213> ORGANISM: Artificial
<220> FEATURE:
<223> OTHER INFORMATION: Recognition Site

<400> SEQUENCE: 31 gtttaaac                                                                  8

<210> SEQ ID NO 32
<211> LENGTH: 6
<212> TYPE: DNA
<213> ORGANISM: Artificial
<220> FEATURE:
<223> OTHER INFORMATION: Recognition Site
<220> FEATURE:
<221> NAME/KEY: misc_feature
<222> LOCATION: (1)..(1)
<223> OTHER INFORMATION: R = G or A

<400> SEQUENCE: 32 rccggy                                                                    6

<210> SEQ ID NO 33
<211> LENGTH: 6
<212> TYPE: DNA
<213> ORGANISM: Artificial
<220> FEATURE:
<223> OTHER INFORMATION: Recognition Site

<400> SEQUENCE: 33 tccgga                                                                    6

<210> SEQ ID NO 34
<211> LENGTH: 6
<212> TYPE: DNA
<213> ORGANISM: Artificial
<220> FEATURE:
<223> OTHER INFORMATION: Recognition Site

<400> SEQUENCE: 34 ttcgaa                                                                    6
```

METHODS FOR DETERMINING CYTOSINE METHYLATION IN DNA AND USES THEREOF

CROSS-REFERENCE TO RELATED APPLICATIONS

This application is a U.S. national stage entry under 35 U.S.C. §371 of PCT International Patent Application No. PCT/US2008/006387, filed May 19, 2008, and claims priority to U.S. Provisional Patent Application No. 60/936,691, filed Jun. 20, 2007, the contents of which are incorporated herein by reference in their entirety.

STATEMENT OF GOVERNMENT SUPPORT

This invention was made with government support under grant number R03 CA111577 awarded by the National Institutes of Health (NCI). The government has certain rights in this invention.

FIELD OF THE INVENTION

The invention is directed to methods of determining the pattern of cytosine methylation in a deoxyribonucleic acid (DNA) specimen, which involve comparing the amount of DNA fragments generated by a methylation-sensitive restriction enzyme with the amount of DNA fragments generated by a methylation-insensitive isoschizomer of the methylation-sensitive restriction enzyme. The methods can be used, for example, for detection of cancer.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Methylation of cytosine in DNA is a major component of epigenetic regulation of gene expression. Cytosine methylation is important for normal growth and development (Dean et al., 2005; Monk et al., 1987) and is a major source of gene expression abnormalities in cancer (Fiegl and Elmasry, 2007; Zhu and Yao, 2007). DNA cytosine methylation can be used as a biomarker for cancer detection (Belinsky, 2004; Gonzalgo et al., 2007; Jubb et al., 2003; Zhu and Yao, 2007). Cytosine methylation may also play a role in regulating the induction of synaptic plasticity in the mature central nervous system (Levenson et al., 2006).

Various approaches have been used to analyze cytosine methylation (Ching et al. 2005; Hu et al. 2005; Khulan et al. 2006; Laird 2003; Ushijima 2005; Weber et al. 2005). Many of the techniques used to test cytosine methylation at multiple loci are not suitable for comparing methylation levels at different loci within a genome. There is a need for a platform for intragenomic profiling that will permit integrating studies of cytosine methylation with other whole-genome studies of epigenetic regulation.

The use of restriction enzymes that are sensitive to cytosine methylation has allowed many of the early insights into the distribution of methylated CpG dinucleotides in the mammalian genome. For example, the use of HpaII revealed that most of the genome remains high molecular weight following digestion despite the short recognition motif (5'-CCGG-3') at which the enzyme cuts (Singer et al. 1979). It was subsequently recognized that between 55 and 70% of HpaII sites in animal genomes are methylated at the central cytosine (Bestor et al. 1984; Bird 1980), which is part of a CpG dinucleotide. The minority of genomic DNA that cuts to a size of hundreds of basepairs was defined as HpaII Tiny Fragments (HTFs) (Bird 1986), revealing a population of sites in the genome at which two HpaII sites are close to each other and both unmethylated on the same DNA molecule. Cloning and sequencing of these HTFs revealed them to be (G+C) and CpG dinucleotide-rich, allowing base compositional criteria to be created to predict presumably hypomethylated CpG islands (Gardiner-Garden and Frommer 1987). Genome sequencing project data have revealed that fewer than 12% of HpaII sites in the human genome (and fewer than 9% in mouse) are located within annotated CpG islands (Fazzari and Greally 2004). This raised the question whether a substantial proportion of HTFs is, in fact, derived from non-CpG island sequences and could be used to examine many non-CpG island sites in the genome for cytosine methylation status.

Most restriction enzyme-based or affinity-based techniques are designed to identify enriched methylated DNA regions in the genome. As most CG dinucleotides of animal genomes are methylated (Gruenbaum et al., 1981; Kunnath and Locker, 1982), including most transposable elements (Yoder et al., 1997), these approaches enrich the majority of the genome and repetitive sequences rather than the hypomethylated minority of unique sequences that tend to be located at functionally-interesting sites. The presence of a hypomethylated site in an assay that enriches methylated DNA has to be inferred from the absence of signal, which can also occur due to technical problems or base compositional reasons.

The approach described in the present application allows the positive identification of hypomethylated loci and is robust for analysis of CG dinucleotide-enriched regions of the genome where restriction enzyme digestion can create short DNA fragments that can pose problems for analysis.

SUMMARY OF THE INVENTION

The present invention provides methods for determining the pattern of cytosine methylation in a DNA specimen by comparing the amount of DNA fragments generated by a methylation-sensitive restriction enzyme with the amount of DNA fragments generated by a methylation-insensitive isoschizomer of the methylation-sensitive restriction enzyme, the methods comprising:

(a) digesting a first sample of the DNA specimen using the methylation-sensitive restriction enzyme to create DNA fragments representing regions of incomplete cytosine methylation in the DNA specimen, wherein restriction enzyme digestion creates double-stranded DNA fragments;

(b) annealing a plurality of pairs of single-stranded oligonucleotides to each other to form a plurality of double-stranded adaptors; wherein different pairs of oligonucleotides have different nucleotide sequences than other pairs of oligonucleotides;

(c) ligating the adaptors formed in step (b) to the ends of the DNA fragments created in step (a) to form continuous nucleic acid sequences of the DNA fragments flanked by adaptors on each end of the DNA fragments, wherein a first proportion of the DNA fragments is flanked by adaptors having identical nucleotide sequences and a second proportion of the DNA fragments is flanked by adaptors having non-identical nucleotide sequences;

(d) quantifying the amount of DNA fragments from step (c) of different lengths as a function of their location in the genome from which the DNA specimen was derived;

(e) digesting a second sample of the DNA specimen using the methylation-insensitive isoschizomer of the methylation-sensitive restriction enzyme to create DNA fragments representing the total potential repertoire of DNA fragments that would be created by the methylation-sensitive restriction enzyme in the absence of cytosine methylation at that restriction enzyme target site in the DNA specimen, wherein restriction enzyme digestion creates double-stranded DNA fragments;

(f) ligating the adaptors formed in step (b) to the ends of the DNA fragments created in step (e) to form continuous nucleic acid sequences of the DNA fragments flanked by adaptors on each end of the DNA fragments, wherein a first proportion of the DNA fragments is flanked by adaptors having identical nucleotide sequences and a second proportion of the DNA fragments is flanked by adaptors having non-identical nucleotide sequences;

(g) quantifying the amount of DNA fragments from step (f) of different lengths as a function of their location in the genome from which the DNA specimen was derived; and (h) comparing the relative amounts of the DNA fragments from step (d) with the DNA fragments from step (g) to determine the pattern of cytosine methylation at the restriction enzyme target sites in the DNA specimen, as a function of their location in the genome from which the DNA specimen was derived, wherein increases in the amount of DNA fragments from step (d) relative to step (g) indicates less cytosine methylation of the DNA fragments from step (d).

DETAILED DESCRIPTION OF THE INVENTION

Figure 1:
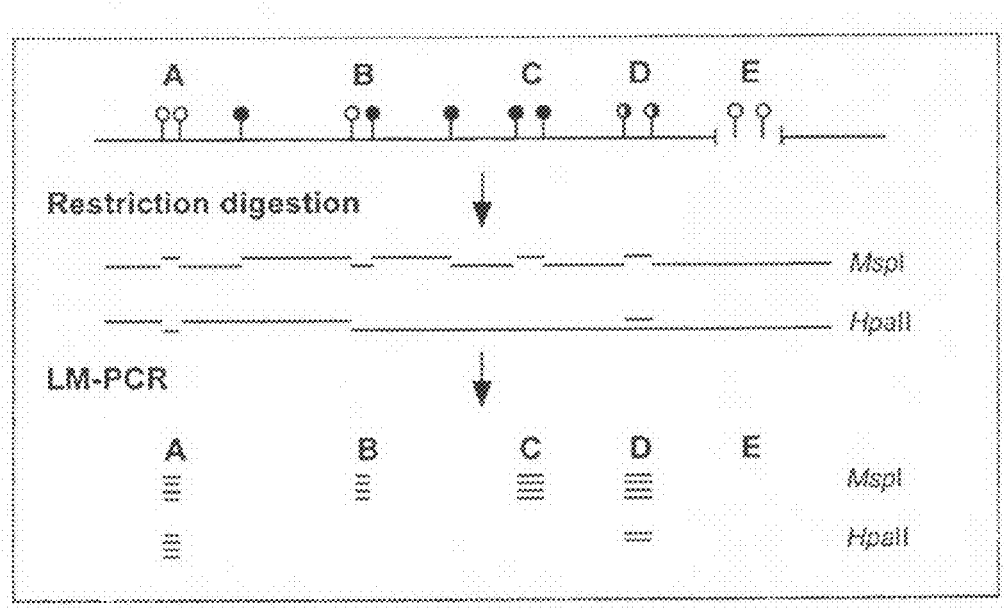
FIG. 1. Principle of the assay. The assay is based on a comparison of representations from DNA following digestion by a methylation-sensitive restriction enzyme, such as HpaII, and its methylation-insensitive isoschizomer, such as MspI. The MspI representation is the total potential population of sites that could be generated by the HpaII representation were none of these sites to be methylated. However, as 55-70% of these sites are methylated in animal genomes (Bestor et al. 1984; Bird 1980), the HpaII representation will always represent a subset of the MspI representation. By comparing the relative representation at individual loci, assignment can be made of cytosine methylation status. While loci such as A should be amplified in both the HpaII and MspI representations, the failure of HpaII to digest both sites at loci B and C will yield a representation from MspI alone, while the partial methylation depicted at locus D should generate a lower HpaII/MspI ratio than at locus A. If a locus is deleted (or has a sequence change at the enzyme cleavage sites) as shown at E, neither representation will generate the locus.

Methods are provided as described herein below for determining the pattern of cytosine methylation in a DNA specimen by comparing the amount of DNA fragments generated by a methylation-sensitive restriction enzyme with the amount of DNA fragments generated by a methylation-insensitive isoschizomer of the methylation-sensitive restriction enzyme.

The standard abbreviations for nucleotide bases are used as follows: adenine (A), cytosine (C), guanine (G), thymine (T) and uracil (U); the letters "A", "C", "G", "T" and "U" are also used to represent the whole nucleotide containing the respective base. The "3'" end of an oligonucleotide has a free hydroxyl group at the 3' carbon of a sugar in the oligonucleotide. The "5'" end of an oligonucleotide has a free hydroxyl or phosphate group at the 5' carbon of a sugar in the oligonucleotide.

As used herein, "anneal" or "annealing" is a biochemical process by which two complementary nucleic acid strands are bound together by hydrogen bonds so as to form perfect base pairs. "Complementary" nucleotides or nucleic acid sequences are those that can form a perfect base pair, where "A" pairs with "T" or "U", and "C" pairs with "G". "Ligate" or "ligating" refers to a biochemical process by which two double-stranded nucleic acid molecules are bound together end to end by enzymatic hydrolysis so as to form a tandemly continuous molecule. "Hybridization" means the association of two complementary nucleic acid strands to form a double stranded molecule.

As used herein, the term "isoschizomer" means pairs of restriction enzymes that recognizes the same target DNA sequence and cleave it in the same way. An example of an isoschizomer pair is the enzyme pair HpaII and MspI, which recognize the DNA sequence 5'-CCGG-3'. HpaII is a methylation-sensitive restriction enzyme that cuts the sequence 5'-CCGG-3' only when the second cytosine ("C") is unmethylated and not when it is methylated. MspI is a methylation-insensitive isoschizomer that cuts the sequence 5'-CCGG-3' independently of whether the second C is methylated or not. HpaII and MspI are a preferred isoschizomer pair.

Additional isoschizomer enzyme pairs that can be used with the present invention are shown in the Table 1.

TABLE 1

Isoschizomer enzyme pairs

| Recognition site | Methylation-insensitive | Methylation-sensitive | SEQ ID NO: |
|---|---|---|---|
| CCGG | MspI | HpaII | 5 |
| ACCGGT | CspAI | AgeI | 6 |
| CACgNcGTC | DraIII | AdeI | 7 |
| CCCGGG | XmaI | SmaI | 8 |
| CCGCTC | BsrBI | MbiI | 9 |
| CYCGRG | BsoBI | AvaI | 10 |
| GANNNNTTC | XmnI | PdmI | 11 |
| GACGTC | ZraI | AatII | 12 |
| GAGCTC | SacI | EcI136II | 13 |
| GAGTC | MlyI | PleI | 14 |
| GATC | CfuI | DpnI | 15 |
| GAWTC | TfiI | PfeI | 16 |
| GCNGC | BsoFI | SatI | 17 |
| GCgGC | BsoFI | Fnu4HI | 18 |
| GCNNNNNNNGC | MwoI | HpyF10VI | 19 |
| GCTAGC | BmtI | NheI | 20 |
| GGCC | HaeIII | NgoPII | 21 |
| GGCGCC | NarI | SfoI | 22 |
| 3'-CCCTG | FaqI | BsmFI | 23 |
| GGNNCC | BspLI | NlaIV | 24 |
| GGTACC | KpnI | Asp718I | 25 |
| GGWCC | AflI | Eco47I | 26 |
| GRCGYC | BsaHI | AhaII | 27 |
| GTAC | Csp6I | RsaI | 28 |
| GTCTC | Alw26I | BsmAI | 29 |
| 3'-CAGAG | BsmAI | Alw26I | 30 |
| GTTTAAAC | MssI | PmeI | 31 |
| RCCGGY | BssAI | BsrFI | 32 |
| TCCGGA | AccIII | MroI | 33 |
| TTCGAA | SfuI | NspV | 34 |

Y = C/T, R = G/A, N = A/C/G/T, W = A/T. The critical cytosine for methylation is marked in bold in Table 1. Lower case nucleotides refer to positions where the restriction enzyme will cut when other mucleotides occupy the same position, but methylation sensitivity occurs when the nucleotide shown is present. All sequences in Table 1 are shown in 5' to 3' orientation unless otherwise indicated. Information on isoschizomers can be obtained from The Restriction Enzyme Database (http://rebase.neb.com).

The invention provides a method for determining the pattern of cytosine methylation in a DNA specimen by comparing the amount of DNA fragments generated by a methylation-sensitive restriction enzyme with the amount of DNA fragments generated by a methylation-insensitive isoschizomer of the methylation-sensitive restriction enzyme, the method comprising:

(a) digesting a first sample of the DNA specimen using the methylation-sensitive restriction enzyme to create DNA fragments representing regions of incomplete cytosine methylation in the DNA specimen, wherein restriction enzyme digestion creates double-stranded DNA fragments;

(b) annealing a plurality of pairs of single-stranded oligonucleotides to each other to form a plurality of double-stranded adaptors; wherein different pairs of oligonucleotides have different nucleotide sequences than other pairs of oligonucleotides;

(c) ligating the adaptors formed in step (b) to the ends of the DNA fragments created in step (a) to form continuous nucleic acid sequences of the DNA fragments flanked by adaptors on each end of the DNA fragments, wherein a first proportion of the DNA fragments is flanked by adaptors having identical nucleotide sequences and a second proportion of the DNA fragments is flanked by adaptors having non-identical nucleotide sequences;

(d) quantifying the amount of DNA fragments from step (c) of different lengths as a function of their location in the genome from which the DNA specimen was derived;

(e) digesting a second sample of the DNA specimen using the methylation-insensitive isoschizomer of the methylation-sensitive restriction enzyme to create DNA fragments representing the total potential repertoire of DNA fragments that would be created by the methylation-sensitive restriction enzyme in the absence of cytosine methylation at that restriction enzyme target site in the DNA specimen, wherein restriction enzyme digestion creates double-stranded DNA fragments;

(f) ligating the adaptors formed in step (b) to the ends of the DNA fragments created in step (e) to form continuous nucleic acid sequences of the DNA fragments flanked by adaptors on each end of the DNA fragments, wherein a first proportion of the DNA fragments is flanked by adaptors having identical nucleotide sequences and a second proportion of the DNA fragments is flanked by adaptors having non-identical nucleotide sequences;

(g) quantifying the amount of DNA fragments from step (f) of different lengths as a function of their location in the genome from which the DNA specimen was derived; and (h) comparing the relative amounts of the DNA fragments from step (d) with the DNA fragments from step (g) to determine the pattern of cytosine methylation at the restriction enzyme target sites in the DNA specimen, as a function of their location in the genome from which the DNA specimen was derived, wherein increases in the amount of DNA fragments from step (d) relative to step (g) indicates less cytosine methylation of the DNA fragments from step (d).

Depending on the restriction enzyme, the DNA specimen can be cleaved to form double-stranded fragments with blunt ends having no overhang or fragments where on the ends one strand of DNA is longer than the other strand thereby creating fragments with overhanging ends. Thus, the double-stranded DNA fragments created in steps (a) and (e) can be fragments having blunt ends or fragments where at both ends of the fragments one strand of DNA is longer than the other strand thereby creating an overhanging end on each end of the DNA fragments.

If the DNA fragments created in step (a) have overhanging ends, then preferably step (b) involves annealing a plurality of pairs of single-stranded oligonucleotides to each other to form a plurality of double-stranded adaptors having an overhanging end that is complementary to the nucleotide sequence of the overhanging ends of the DNA fragments created by restriction enzyme digestion; wherein different pairs of oligonucleotides have different nucleotide sequences than other pairs of oligonucleotides.

In one example, the method is performed by annealing a first pair of oligonucleotides to each other to form a first adaptor; and annealing a second pair of oligonucleotides to each other to form a second adaptor, wherein the second pair of oligonucleotides has a different nucleotide sequence than the first pair of oligonucleotides. The first pair of oligonucleotides and the second pair of oligonucleotides can be present in equal amounts or in different amounts. The ends of the DNA fragments can be blunt ends or overhanging ends. Preferably, if the DNA fragments have overhanging ends, the double-stranded adaptors have an end that is complementary to the nucleotide sequence of the ends of the DNA fragments.

The method can also be performed by, for example:

annealing a first pair of oligonucleotides to each other to form a first adaptor;

annealing a second pair of oligonucleotides to each other to form a second adaptor, wherein the second pair of oligonucleotides has a different nucleotide sequence than the first pair of oligonucleotides; and annealing a third pair of oligonucleotides to each other to form a third adaptor, wherein the third pair of oligonucleotides has a different nucleotide sequence than the first and second pairs of oligonucleotides. The first pair of oligonucleotides, the second pair of oligonucleotides and the third pair of oligonucleotides can be present in equal amounts or in different amounts. The ends of the DNA fragments can be blunt ends or overhanging ends. Preferably, if the DNA fragments have overhanging ends, the double-stranded adaptors have an end that is complementary to the nucleotide sequence of the ends of the DNA fragments.

Preferably, the oligonucleotides are at least 10 nucleotides in length or at least one of the oligonucleotides is at least 10 nucleotides in length.

Preferably, the formation of a continuous nucleic acid sequence of a DNA fragment flanked on each end by adaptors having non-identical nucleotide sequences prevents folding of the DNA fragment back upon itself and annealing between complementary adaptor sequences. This is particularly important when the DNA fragment is less than 200 basepairs in length.

Preferably, the use of a plurality of different adaptors increases the number of loci that can be examined in a DNA sample by at least 50% over the number of loci that can be examined using only a single type of adaptor.

In steps (c) and (f), the methods can further comprise annealing the adaptors to the ends of the DNA fragments prior to ligation.

The amounts of the DNA fragments can be quantified using DNA sequencing or using polymerase chain reaction (PCR) amplification and microarray analysis. Preferably, PCR amplification selectively amplifies DNA fragments less than 2000 basepairs in length. Preferably, PCR amplification is carried out using a $Mg^{2+}$ concentration of 1-3 mM and more preferably at a $Mg^{2+}$ concentration of 2 mM. Preferably, PCR amplification is carried out using betaine to improve melting of DNA. Preferably, betaine is used at a concentration of about 1 molar.

The method can further comprise hybridizing probes to the DNA fragments to a microarray of oligonucleotides representing specific loci of the DNA specimen. Preferably, the loci are located at regions of DNA that are rich in restriction enzyme recognition sites. Preferably, the loci are located at gene promoter sites.

The DNA specimen can be genomic DNA. The DNA specimen can be from a specific tissue, such as for example, skeletal muscle, cardiac muscle, smooth muscle, kidney, bladder, lung, liver, brain, pancreas, spleen, eye, skin, bone, hair, breast, ovary, prostate, esophagus, stomach, intestines, colon, rectum, glia, central nervous system tissue, or peripheral nervous system tissue. The DNA specimen can be obtained from blood, urine, stool, sputum or saliva.

The DNA can be from a subject such as a mouse, rat, cat, dog, horse, sheep, cow, steer, bull, livestock, or a primate such as a monkey or human. Preferably, the subject is a human. The DNA specimen can be obtained from a subject having a disease or from a subject suspected of having a disease, such as, for example, a developmental disease or a cancer such as e.g. breast cancer or colon cancer.

The methods disclosed herein can be used to investigate any cellular response to the environment, i.e., any change in cellular or organismal phenotype in any organism that methylates its genome, in any cell type from those organisms, at any age (as methylation can change with age) in males or females (as methylation can differ between sexes).

The methods described herein provide for intragenomic profiling of cytosine methylation and for intergenomic comparisons of cytosine methylation.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Overview

The present technique is based on HpaII Tiny Fragment (HTF) enrichment by ligation-mediated PCR, creating the acronym HELP. HELP enrichment, used as part of comparative isoschizomer profiling and in combination with customized genomic microarrays, allows robust intragenomic profiling of cytosine methylation. The principle of the method is shown in FIG. 1. Previously, ligation-mediated polymerase chain reaction (LM-PCR) was used to amplify DNA fragments in the size range from 200-2,000 base pairs (bps), with little amplification of DNA of less than 200 bp (Khulan et al., 2006). These shorter fragments (between two CCGG motifs) occur more frequently in CG dinucleotide-enriched regions. The technique described herein allows robust amplification of DNA fragments of ≤50 bp to 2,000 bp. This increases the number of loci that can be amplified in the genome from 1,016,980 to 1,531,367, which allows increased density of coverage of gene promoters and CG dinucleotide-enriched regions. The performance of this protocol has been illustrated using the human lymphocyte GM06990 cell line and a microarray representing the 1% of the human genome studied by the ENCODE consortium (ENCODE consortium, 2004).

Materials and Methods

Isoschizomer enzymes. HpaII and MspI were obtained from New England BioLabs.

Cell preparation and DNA purification. GM06990 B lymphocytes were cultured in RPMI 1640 with 15% FBS, 1% Glutamine and antibiotics. The cells were harvested and washed twice by PBS and stored in −70 C. To extract DNA, the cells were suspended in 10 ml of 10 mM Tris-HCL (pH 8.0)/0.1M EDTA and 1 ml of 10% SDS and 10 ul of RNaseA (20 mg/ml) was added. After incubation for 1 hr at 37° C., 50 μl of proteinase K (20 mg/ml) was added, and the solution was gently mixed and incubated in 50° C. waterbath overnight. The lysate was treated by saturated phenol three times and chroloform twice, and dialyzed with 0.2×SSC. The 0.2×SSC was changed three times in 16 hours at 4° C. The dialysis bags were dehydrated by polyethylene glycol. The purity and amount of DNA was checked by spectrometry (Nanodrop, Wilmington, Del.).

Assay with a two adaptor/primer set. The following primers were used:

```
BK12:
5'-CGGCTGTTCATG-3',           (SEQ ID NO: 1)

BK24:
5'-CGACGTCGACTATCCATGAACAGC-3',  (SEQ ID NO: 2)

MO12:
5'-CGGCTTCCCTCG-3',           (SEQ ID NO: 3)
and

MO24:
5'-GCAACTGTGCTATCCGAGGGAAGC-3'.  (SEQ ID NO: 4)
```

Five μg of genomic DNA was digested by either HpaII or MspI and purified by phenol/chroloform extraction and ethanol precipitation. Each 1 μg of digested genomic DNA was ligated by T4 DNA ligase with four oligos (each 3.7 μl JHpaII12 and NHpaII12 (6 OD/ml), JHpaII24 and NHpaII24 (12 OD/ml)) in a final volume of 33 μl. The ligated genomic fragments were diluted and used as the template for the LM-PCR. The optimization of polymerase chain reaction (PCR) condition for ligation-mediated (LM-PCR) was performed as shown in the results section, using standard PCR conditions with/without betaine or dimethyl sulfoxide. PCR products were assessed by gel electrophoresis and purified using a PCR purification kit (Qiagen). The concentration of PCR products were measured by spectrometry. The intensities of DNA from gel images were processed using ImageJ and Photoshop.

Microarray design, hybridization and data analysis. The microarrays were designed to represent loci amplified by the LM-PCR reaction. The size range of product was 200-2,000 base pair (bp), so an in silico digest was conducted with HpaII (CCGG), and all sequence fragments of the appropriate size range were retained. An initial probe set was generated by selecting a 50-mer oligo every ten base pairs, avoiding repeat-masked regions and sequence containing ambiguities. A measure of small oligo frequency was determined by sliding a 15-mer window along the length of each 50-mer oligo and determining the average frequency. The uniqueness of each 50-mer was determined by looking for perfect matches using SSAHA2 (Ning et al. 2001). Ten 50-mer oligonucleotides were selected to represent each HpaII fragment using a score based selection algorithm based on three primary parameters: average 15-mer frequency, 50-mer count, and base pair composition rules. The base pair composition rules add penalties for homopolymer runs; stretches of more than 3 G's or C's, or more than 5 A's or T's, are penalized, with larger penalties for longer stretches. After the first oligo is selected, an additional positional parameter is added to encourage uniform distribution of subsequent oligos along the length of the fragment.

Microarrays of oligonucleotides were printed using maskless array synthesis (Nuwaysir et al. 2002) in the NimbleScreen 12 format (NimbleGen Systems Inc, Madison, Wis.). The LM-PCR products were labeled for microarray analysis as previously described (Selzer et al. 2005) using Cy3 or Cy5-conjugated oligonucleotides and random primers. The HpaII and MspI representations were co-hybridized to the microarray in the NimbleGen Service Laboratory and scanned to quantify the 532 and 635 nm fluorescence at each oligonucleotide on the microarray.

Each co-hybridization was analyzed by visual inspection of the image file to ensure that the signals were uniform. Each fragment represented on the microarray consists of 10 separate oligonucleotide probes, each with an associated signal intensity. The median signal intensity was calculated for each fragment to define the fragment's signal intensity. The HpaII and MspI signal intensities were correlated and plotted against each other or fragment length using the R statistical package (http://www.r-project.org/). Branching dendrograms were generated based on an epigenomic distance measurement of (1-correlation coefficient) and plotted using MatLab. The frequencies of loci with different HpaII signal intensities were modeled using a mixed Gaussian model (one variant) to separate loci into groups with 90% or 10% probabilities of being in the group of low intensity signals, defining categories 1 and 2, the remainder of the loci with higher signal intensities categorized as group 3. The range of intensities for group 1 was used as a measure of variability between arrays. Normalization was performed by subtracting the mean log ratio of this group of signal intensities in order to center log ratios over the entire array. Data were generated using the normalized HpaII/MspI log ratios for the three biological replicates in one array.

Computational calculation of MspI fragments and annotations. The start and end position of MspI fragments were computationally calculated from the hg17 assembly of the human genome sequence at the UCSC Genome Browser (genome.ucsc.edu), and the sequence characteristics ((C+G) mononucleotide percent, CG dinucleotide frequency per 1 kb) and overlaps with CpG islands, CG clusters, retroelement and the 1 kb upstream region of refSeq genes were examined.

Results

Figure 2:
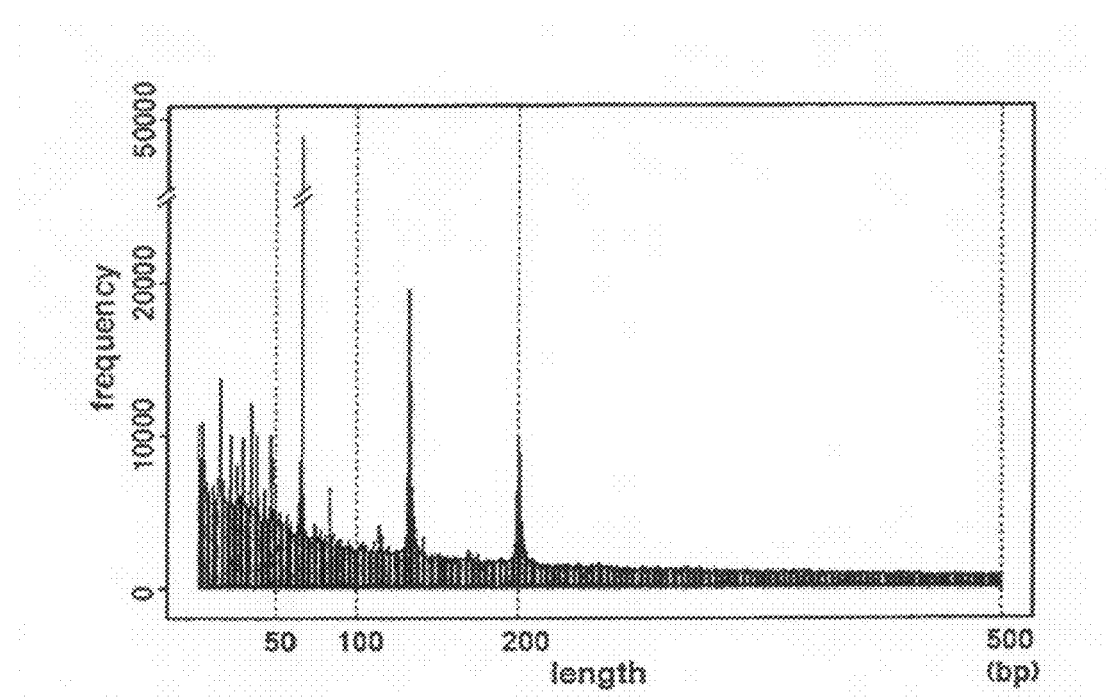
FIG. 2. In silico analysis of length and frequencies of human MspI fragments. The frequencies of the fragments computationally generated from human genome sequence were plotted by length as a frequency histogram. Note that the frequency is higher in the shorter fragments. Three peaks (69, 135-6 and 203-4 bp) are related to the Alu species (mainly AluS and AluY) and also observed in the EtBr staining of the MspI reference representation in FIG. 3.

To assess the value of an expanded size range for HELP representations, the frequencies of HpaII/MspI fragments from the human genome sequence were calculated by in silico-digesting at CCGG sites and measuring the size and frequency of the fragments generated. The size distribution of these HpaII/MspI fragments is skewed strongly towards shorter fragments (FIG. 2). This demonstrates that the previous failure to amplify fragments of <200 bp (Khulan et al. 2006) occurred despite their abundance in the genome, indicating the shortcomings of the previous original genomic representation technique. Of the MspI fragments in the human genomic sequence, 44.5% of fragments in the 200-2000 bp range are represented in the assay of Khulan et al. 2006, while the 22.5% in the 50-200 bp range were not generated using that protocol. As long oligonucleotides are used for the microarrays for HELP assays, 50 bp represents a practical lower limit of fragment sizes that can be interrogated. By expanding the size range of the genomic representation to 50-2,000 bp, the number of loci that could be studied in the genome can be increased by approximately 50%, increasing representation in the most CG-dense regions in particular.

Figures 3A, 3B, 3C, 3D:
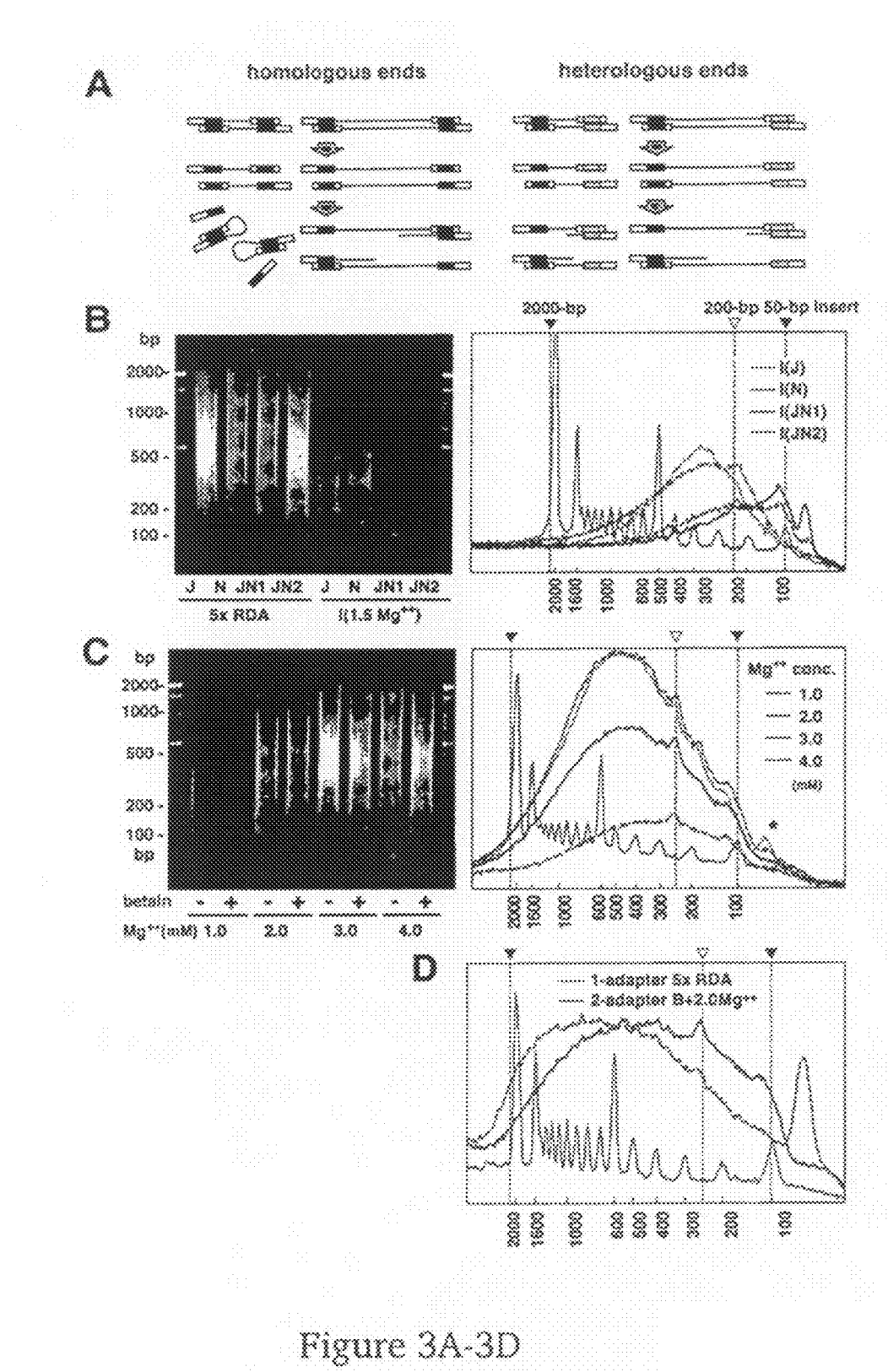
FIG. 3A-3D. Two-linker strategy and PCR amplification. A) Two linker strategy. Homologous ends using a single adaptor can produce a hairpin structure in short fragments, an event that should be reduced by 50% using dual adaptors to create heterologous ends. B) The effect of the two linker set on the PCR product. The product using single adaptors shows similar size distributions for both JHpaII (J) and NHpaII (N). The product of dual adaptors (JN1, JN2) shows a broader size range of products using 5×RDA (R) buffer. In the standard buffer containing 1.5 mM MgCl (I, 1.5 Mg++), the change of size distribution was more significant. C) Optimization of the PCR buffer for short fragment amplification. The amount of PCR product was increased by increasing the $Mg^{2+}$ concentration. Note that with the higher $Mg^{2+}$ concentration and without betaine, putative primer dimers were observed.

Two possibilities were considered most likely to contribute to the failure of Khulan et al. (2006) to represent DNA fragments of <200 bp. First, it was tested whether regions containing HpaII/MspI CCGG sites at higher frequency are enriched in (C+G) mononucleotide content, making them difficult to amplify by conventional PCR techniques. The (C+G) mononucleotide content of the HpaII/MspI fragments of 50-2,000 bp was found to be 60.0%, in contrast to the 47.7% for 200-2,000 bp fragments. Secondly, the presence of ligated adapter sequence may cause self-annealing preferentially for shorter fragments, preventing PCR amplification of these annealed hairpin structures (FIG. 3A). Two adaptors were used for the ligation step to test whether hairpin formation was occurring and causing poor amplification. This provides the ligated product with heterologous ends at 50% frequency (FIG. 3A), preventing intramolecular annealing. Each adapter on its own shows failure of amplification of fragments <200 bp, but the use of two adapters and corresponding primers markedly changes the size distribution of amplified fragments to generate much smaller molecules (FIG. 3B). Since this change was more marked when using the standard buffer supplied with the Taq polymerase (20 mM Tris-HCl (pH 8.4), 50 mM KCl) rather than the 5×RDA buffer used by Khulan et al. (2006), the standard buffer was used for further optimization.

These improvements in size range representation came at the expense of yield and with the generation of primer-dimers. To solve these problems, higher concentrations of magnesium were used, finding that yield and primer-dimer concentrations were both increased, but that at 4.0 mM $Mg^{2+}$ there was a selective loss in amplification of shorter PCR products. Betaine was also used as a means of improving the amplification of (G+C)-rich templates (Henke et al., 1997). Using 1.0 M betaine, primer-dimer formation was reduced even with higher $Mg^{2+}$ concentrations while preserving amplification of short fragments (FIG. 3C). Dimethyl sulfoxide was also tested with and without betaine, but this failed to enhance short fragment amplification (data not shown). The final set of optimized conditions uses a $Mg^{2+}$ concentration of 2.0 mM with 1.0 M betaine. The amplification products shown in FIG. 3C include the adapter sequences (~50 bp), indicating that products ≤50 bp in size are being amplified while preserving the ability to amplify up to 2,000 bp. Interestingly, within the amplified MspI representation 'bands' of strong signal intensity were observed that correspond to the over-represented fragment sizes from FIG. 2, which correspond in turn to Alu SINE sequences in the human genome.

Figures 4A, 4B, 4C:
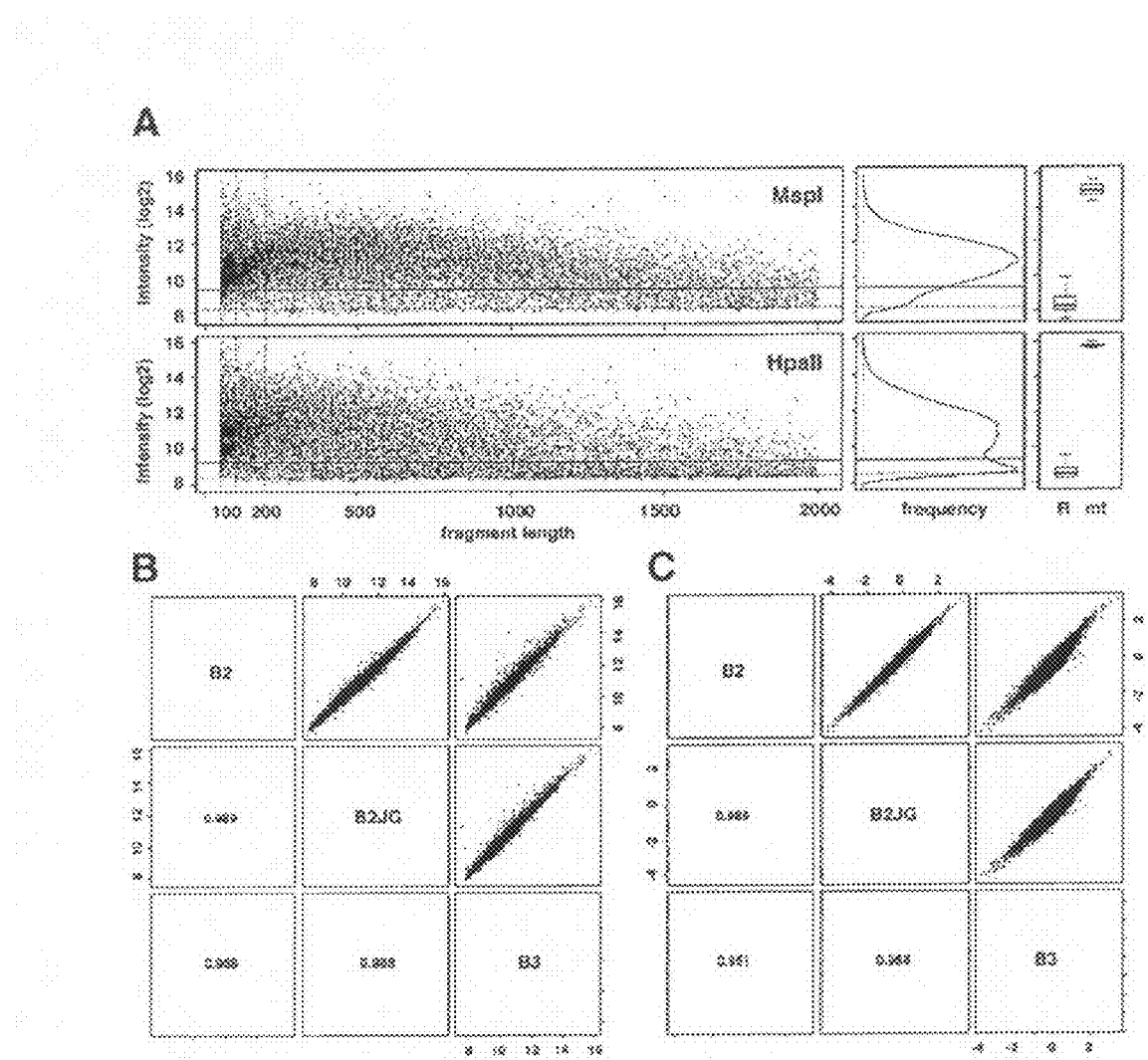
FIG. 4A-4C. Hybridization result of two linker PCR HELP product. A) Size and intensity plot of MspI and HpaII representations. Dashed lines indicate the median value of random control probes and solid lines show the 2.5 median absolute deviations (MAD) calculated from the random probe intensities. Note that the intensities of most probes in the MspI representation less than 200 bp in length are higher than the 2.5 MAD line, indicating the efficient representation of shorter fragments. B) Inter-array correlation plot of MspI representation. One technical and two biological replicates show high correlation values. C) Inter-array correlation plot of HpaII/MspI ratio values.

It was next determined whether the shorter fragments generated could be labeled and hybridized to a microarray as successfully as the larger size range previously described (Khulan et al., 2006). A microarray was custom-designed using oligonucleotides for each of the 18,529 HpaII/MspI fragments of 50-2,000 bp in the ENCODE regions of the genome (ENCODE consortium, 2004). HpaII and MspI representations were generated from the GM06990 cell line using the conditions above, confirming the larger size range in each representation by gel electrophoresis (data not shown). These representations were labeled by random priming and co-hybridized to the microarray, to test the outcome in terms of the signal intensities obtained for each fragment size. As there was no appreciable difference between the use of random heptamers and nonamers (data not shown), data are presented only for the latter in FIG. 4. The background fluorescence level was defined using a set of 10,100 oligonucleotides representing random sequences, applying a threshold of 2.5 median absolute deviations above the median intensity of these control oligonucleotides (2.5 MAD). This value consistently defines the distinctive population of loci in HpaII representations that do not amplify due to methylation at those sites (see FIG. 4A; HpaII). The same threshold was used to define signal intensities in the MspI channel indicating loci that have failed to amplify adequately (see FIG. 4A; MspI). The MspI representation is used to test the performance of the protocol, as it is insensitive to cytosine methylation and should generate all of the fragments represented on the microarray. In the current experiment, a failure rate of 5-9% was observed, but only 2-4% were in the size range of 50-199 bp (Table 2). The labeling and hybridization of the additional representation of short fragments is as efficient as for the size range 200-2,000 bp. When the HpaII representation was studied, the typical bimodal distribution representing methylated and unmethylated loci was observed, demonstrating that the ability to perform this discrimination is preserved using the present protocol (FIG. 4A).

It was then determined whether the addition of fragments from the smaller size range had any effect to compromise reproducibility. Scatterplots and Pearson's correlation coefficients for $log_2$ MspI intensities and HpaII/MspI intensity ratios are illustrated in FIGS. 4B,C. Both technical and biological replicates show high correlation in MspI intensities (98-99%, FIG. 4B) and HpaII/MspI ratios (95-99%, FIG. 4C), demonstrating that the amplification of each fragment remains reproducible in this protocol.

Analysis of the sequences represented by representations of different by ranges was performed computationally. The proportion of CpG islands represented by the present technique increases to 98.5%, compared to 87.0% using the protocol of Khulan et al. (2006), with a concurrent increase in the mean number of fragments per CpG island (from 1.6 to 5.5). An alternative annotation of CG clusters is also represented more comprehensively using the present protocol, increasing from a proportion of 95.1 to 98.6%, and an average representation of 6.3 fragments per locus (from 2.3 fragments). The proportion of transcription start sites (represented by the −1,000-1,000 bp window at each gene) represented by the protocol of Khulan et al. (2006) was 89.1% with an average of 2.6 fragments per promoter. This rises to 91.1% and 6.8 fragments per promoter with the present protocol.

Discussion

Genomic representations by LM-PCR are used by a number of different applications, including representational oligonucleotide microarray analysis (ROMA) (Lucito et al., 2003), high-density SNP microarrays (Matsuzaki et al., 2004) and epigenomic assays testing cytosine methylation (Hatada et al., 2006; Lakshmi et al., 2006; Yuan et al., 2006). The HELP assay uses representations from, for example, HpaII to distinguish methylated from unmethylated loci in the genome, with a concurrent MspI representation used to define the full range of potential HpaII-amplifiable fragments. The more fragments that can be represented, the greater the level of detail that can be described for the epigenome.

The procedures disclosed herein not only generate an increased representation of the genome but also provide greater coverage of loci of particular interest, such as promoters and CpG islands. By in silico analysis, the proportion of coverage for CpG islands as well as for CG cluster approached the maximum (98.5% and 98.6%, respectively). In addition, the mean fragment number for both CpG-rich regions were increased 2- to 3-fold compared with previous coverage. Although the proportional increase in coverage of promoters is slight, the representative fragment number was increased from 2.6 to 6.8 per locus, which enables a more detailed analysis of DNA methylation in these promoter regions.

One valuable benefit of the present procedures is that shorter fragments (50-200 bp) can be labeled and hybridized with the random priming technique. This is one of the few means of objectively testing the influence of fragment length on labeling and hybridization efficiency.

Of the 27.9 million CG dinucleotides in the haploid human genome, only ~7% are within annotated CpG islands, with ~51% within repetitive sequences and the remaining ~42% in non-CpG island unique sequences (Fazzari and Greally, 2004). While most CpG islands are unmethylated (Cooper et al., 1983) and most transposable elements are methylated (Yoder et al., 1997), the status of the remaining CG dinucleotides is not well studied. With 50-75% of CG dinucleotides methylated in animal genomes (Gruenbaum et al., 1981; Kunnath and Locker, 1982), the likelihood is that at least some of these CGs are methylated and may encode loci with methylation that is variable enough to account for this large range of methylation observed in animal genomes. The goal of epigenomics studies is to capture variability in epigenetic patterns so that these can be correlated with phenotypic differences. It is therefore critical that epigenomic assays study the entire epigenome, as the 42% of CGs in unique sequence not annotated as CpG islands may prove to be highly informative, and the ability to predict a priori where epigenomic information is located in the genome is limited. The present assay provides a means of screening a large number of HpaII and other methylation-sensitive isoschizomer sites throughout the genome, defining loci with changes in cytosine methylation that can then be tested using quantitative single-locus techniques. The methods described herein provide for both intragenomic profiling of cytosine methylation and intergenomic comparisons of cytosine methylation.

An immediate disease-related application of genome-wide cytosine methylation assays is to study cancer, in which epigenetic regulation is profoundly disturbed (Jones and Baylin 2002). The use of a methylation-insensitive isoschizomer controls for a common variable in cancer, that of changes in copy number (Lengauer et al. 1998). By reporting the ratio of isoschizomer representations, amplified or deleted regions will generate a measure of cytosine methylation that can be used for intragenomic comparisons with normal, diploid regions, making the present assay exceptionally suited to cancer epigenomic studies. Moreover, given the role of epigenetics in other processes and diseases, such as aging (Fraga et al. 2005), mediation of dietary influences (Wolff et al. 1998) and possibly the sequelae of assisted reproductive technology (Maher et al. 2003), genome-wide cytosine methylation assays are envisioned to find applications beyond the cancer focus.

TABLE 2A

Representation of Human MspI Fragments

| Representation | Size range (bp) | Number | CpG islands over-lapped | % CpG islands represented | CG clusters over-lapped | % CG clusters over-lapped | refSeq promoters (2 kb flanking) over-lapped | % refSeq promoters (2 kb flanking) over-lapped |
|---|---|---|---|---|---|---|---|---|
| Added herein | 50-199 | 514,387 | 3,154 | 11.5% | 1,514 | 3.4% | 375 | 2.0% |
| Khulan et al. (2006) | 200-2000 | 1,016,980 | 23,881 | 87.0% | 42,226 | 95.1% | 16,848 | 89.1% |
| Total | 50-2000 | 1,531,367 | 27,035 | 98.5% | 43,740 | 98.6% | 17,223 | 91.1% |

TABLE 2B

Annotation of Human MspI Fragments

| | N | Y | total | coverage | average fragment number | fold |
|---|---|---|---|---|---|---|
| Previous* CGI | 3,556 | 23,881 | 27,437 | 87.0% | 1.601 | |
| New**_CGI | 402 | 27,035 | 27,437 | 98.5% | 5.497 | 3.433 |
| Previous*_CGc | 2,157 | 42,226 | 44,383 | 95.1% | 2.342 | |
| New**_CGc | 643 | 43,740 | 44,383 | 98.6% | 6.275 | 2.680 |
| Previous*_RS2Kb | 2,055 | 16,848 | 18,903 | 89.1% | 2.602 | |
| New**_RS2Kb | 1,680 | 17,223 | 18,903 | 91.1% | 6.777 | 2.604 |

CGI = CpG islands
CGc = CG clusters
RS2KB = within 2 kilobases flanking transcription start sites of refSeq genes (promoter regions)
*Khulan et al. (2006);
**disclosed herein.

REFERENCES

Belinsky, S. A. Gene-promoter hypermethylation as a biomarker in lung cancer. Nat Rev Cancer. 4(9):707-17, 2004.

Bestor, T. H., S. B. Hellewell, and V. M. Ingram. 1984. Differentiation of two mouse cell lines is associated with hypomethylation of their genomes. *Mol Cell Biol* 4: 1800-1806.

Bird, A. P. 1980. DNA methylation and the frequency of CpG in animal DNA. *Nucleic Acids Res.* 8: 1499-1504.

Bird, A. P. 1986. CpG-rich islands and the function of DNA methylation. *Nature* 321: 209-213.

Ching, T. T., A. K. Maunakea, P. Jun, C. Hong, G. Zardo, D. Pinkel, D. G. Albertson, J. Fridlyand, J. H. Mao, K. Shchors, W. A. Weiss, and J. F. Costello. 2005. Epigenome analyses using BAC microarrays identify evolutionary conservation of tissue-specific methylation of SHANK3. *Nature Genet.* 37: 645-651.

Cooper, D. N., Taggart, M. H., and Bird, A. P. (1983). Unmethylated domains in vertebrate DNA. Nucleic Acids Res 11, 647-58.

Dean W, Lucifero D, Santos F. DNA methylation in mammalian development and disease. Birth Defects Res C Embryo Today. 75(2):98-111, 2005.

ENCODE consortium. (2004). The ENCODE (ENCyclopedia Of DNA Elements) Project. Science 306, 636-40.

Fazzari, M. J. and J. M. Greally. 2004. Epigenomics: beyond CpG islands. *Nature Rev. Genet.* 5: 446-455.

Fiegl, H. and Elmasry, K. Cancer diagnosis, risk assessment and prediction of therapeutic response by means of DNA methylation markers. Dis. Markers 23(1-2): 89-96, 2007.

Fraga, M. F., E. Ballestar, M. F. Paz, S. Ropero, F. Setien, M. L. Ballestar, D. Heine-Suner, J. C. Cigudosa, M. Urioste, J. Benitez, M. Boix-Chornet, A. Sanchez-Aguilera, C. Ling, E. Carlsson, P. Poulsen, A. Vaag, Z. Stephan, T. D. Spector, Y. Z. Wu, C. Plass, and M. Esteller. 2005. Epigenetic differences arise during the lifetime of monozygotic twins. *Proc. Natl. Acad. Sci. USA* 102: 10604-10609.

Gardiner-Garden, M. and M. Frommer. 1987. CpG islands in vertebrate genomes. *J. Mol. Biol.* 196: 261-282.

Gonzalgo M L, Datar R H, Schoenberg M P, Cote R J. The role of deoxyribonucleic acid methylation in development, diagnosis, and prognosis of bladder cancer. Urol Oncol. 25(3):228-35, 2007.

Gruenbaum, Y., Stein, R., Cedar, H., and Razin, A. (1981). Methylation of CpG sequences in eukaryotic DNA. FEBS Lett 124, 67-71.

Hatada, I., Fukasawa, M., Kimura, M., Morita, S., Yamada, K., Yoshikawa, T., Yamanaka, S., Endo, C., Sakurada, A., Sato, M., et al. (2006). Genome-wide profiling of promoter methylation in human. Oncogene 25, 3059-3064.

Henke, W., Herdel, K., Jung, K., Schnorr, D., and Loening, S. A. (1997). Betaine improves the PCR amplification of GC-rich DNA sequences. Nucleic Acids Res 25, 3957-8.

Hu, M., J. Yao, L. Cai, K. E. Bachman, F. van den Brule, V. Velculescu, and K. Polyak. 2005. Distinct epigenetic changes in the stromal cells of breast cancers. *Nature Genet.* 37: 899-905.

Jones, P. A. and S. B. Baylin. 2002. The fundamental role of epigenetic events in cancer. *Nature Rev. Genet.* 3: 415-428.

Jubb A M, Quirke P, Oates A J. DNA methylation, a biomarker for colorectal cancer: implications for screening and pathological utility. Ann NY Acad Sci. 983:251-67, 2003.

Khulan, B., Thompson, R. F., Ye, K., Fazzari, M. J., Suzuki, M., Stasiek, E., Figueroa, M. E., Glass, J. L., Chen, Q., Montagna, C., Hatchwell, E., Selzer, R. R., Richmond, T. A., Green, R. D., Melnick, A., and Greally, J. M. (2006). Comparative isoschizomer profiling of cytosine methylation: the HELP assay. Genome Res 16, 1046-55.

Kunnath, L., and Locker, J. (1982) Characterization of DNA methylation in the rat. Biochim Biophys Acta 699, 264-71.

Laird, P. W. 2003. The power and the promise of DNA methylation markers. *Nature Rev. Cancer* 3: 253-266.

Lakshmi, B., Hall, I. M., Egan, C., Alexander, J., Leotta, A., Healy, J., Zender, L., Spector, M. S., Xue, W., Lowe, S. W., et al. (2006). Mouse genomic representational oligonucleotide microarray analysis: detection of copy number variations in normal and tumor specimens. Proc Natl Acad Sci USA 103, 11234-11239.

Lengauer, C., K. W. Kinzler, and B. Vogelstein. 1998. Genetic instabilities in human cancers. *Nature* 396: 643-649.

Levenson J M, Roth T L, Lubin F D, Miller C A, Huang I C, Desai P, Malone L M, Sweatt J D. Evidence that DNA (cytosine-5) methyltransferase regulates synaptic plasticity in the hippocampus. J Biol Chem. 2006 Jun. 9; 281(23): 15763-73. Epub 2006 Apr. 10.

Lucito R, Healy J, Alexander J, Reiner A, Esposito D, Chi M, Rodgers L, Brady A, Sebat J, Troge J, West J A, Rostan S, Nguyen K C, Powers S, Ye K Q, Olshen A, Venkatraman E, Norton L, Wigler M. Representational oligonucleotide microarray analysis: a high-resolution method to detect genome copy number variation. Genome Res. 2003 October; 13(10):2291-305. Epub 2003 Sep. 15.

Maher, E. R., L. A. Brueton, S. C. Bowdin, A. Luharia, W. Cooper, T. R. Cole, F. Macdonald, J. R. Sampson, C. L. Barratt, W. Reik, and M. M. Hawkins. 2003. Beckwith-Wiedemann syndrome and assisted reproduction technology (ART). *J. Med. Genet.* 40: 62-64.

Matsuzaki H, Dong S, Loi H, Di X, Liu G, Hubbell E, Law J, Berntsen T, Chadha M, Hui H, Yang G, Kennedy G C, Webster T A, Cawley S, Walsh P S, Jones K W, Fodor S P, Mei R. Genotyping over 100,000 SNPs on a pair of oligonucleotide arrays. Nat Methods. 2004 November; 1(2): 109-11.

Monk, M, Boubelik, M and Lehnert, S. Temporal and regional changes in DNA methylation in the embryonic, extraembryonic and germ cell lineages during mouse embryo development. Development 99: 371-382, 1987.

Ning, Z., A. J. Cox, and J. C. Mullikin. 2001. SSAHA: a fast search method for large DNA databases. *Genome Res.* 11: 1725-1729.

Nuwaysir, E. F., W. Huang, T. J. Albert, J. Singh, K. Nuwaysir, A. Pitas, T. Richmond, T. Gorski, J. P. Berg, J. Ballin, M. McCormick, J. Norton, T. Pollock, T. Sumwalt, L. Butcher, D. Porter, M. Molla, C. Hall, F. Blattner, M. R. Sussman, R. L. Wallace, F. Cerrina, and R. D. Green. 2002. Gene expression analysis using oligonucleotide arrays produced by maskless photolithography. *Genome Res.* 12: 1749-1755.

Selzer, R. R., T. A. Richmond, N. J. Pofahl, R. D. Green, P. S. Eis, P. Nair, A. R. Brothman, and R. L. Stallings. 2005. Analysis of chromosome breakpoints in neuroblastoma at sub-kilobase resolution using fine-tiling oligonucleotide array CGH. *Genes Chromosomes Cancer* 44: 305-319.

Singer, J., J. Roberts-Ems, and A. D. Riggs. 1979. Methylation of mouse liver DNA studied by means of the restriction enzymes msp I and hpa II. *Science* 203: 1019-1021.

Ushijima, T. 2005. Detection and interpretation of altered methylation patterns in cancer cells. *Nature Rev. Cancer* 5: 223-231.

Weber, M., J. J. Davies, D. Wittig, E. J. Oakeley, M. Haase, W. L. Lam, and D. Schubeler. 2005. Chromosome-wide and promoter-specific analyses identify sites of differential DNA methylation in normal and transformed human cells. *Nature Genet.* 37: 853-862.

Wolff, G. L., R. L. Kodell, S. R. Moore, and C. A. Cooney. 1998. Maternal epigenetics and methyl supplements affect agouti gene expression in Avy/a mice. *Faseb J.* 12: 949-957.

Yan, P. S., C. M. Chen, H. Shi, F. Rahmatpanah, S. H. Wei, and T. H. Huang. 2002. Applications of CpG island microarrays for high-throughput analysis of DNA methylation. *J. Nutr.* 132: 2430S-2434S.

Yuan, E., Haghighi, F., White, S., Costa, R., McMinn, J., Chun, K., Minden, M., and Tycko, B. (2006). A single nucleotide polymorphism chip-based method for combined genetic and epigenetic profiling: validation in decitabine therapy and tumor/normal comparisons. Cancer Res 66, 3443-3451.

Yoder, J. A., Walsh, C. P., and Bestor, T. H. (1997). Cytosine methylation and the ecology of intragenomic parasites. Trends Genet 13, 335-40.

Zhu, J. and Yao, X. Use of DNA methylation for cancer detection and molecular classification. J Biochem Mol Biol. 40(2):135-41, 2007.

What is claimed is:

1. A method for determining the pattern of cytosine methylation in a DNA specimen by comparing the amount of DNA fragments generated by a methylation-sensitive restriction enzyme with the amount of DNA fragments generated by a methylation-insensitive isoschizomer of the methylation-sensitive restriction enzyme, the method comprising:

(a) digesting a first sample of the DNA specimen using the methylation-sensitive restriction enzyme to create double-stranded DNA fragments of ≤50 bp up to 2000 bp comprising regions of incomplete cytosine methylation in the DNA specimen;

(b) annealing a plurality of pairs of single-stranded oligonucleotides to each other to form a plurality of double-stranded adaptors, wherein different pairs of the plurality of pairs of oligonucleotides have different nucleotide sequences than other pairs of the plurality of pairs of oligonucleotides;

(c) ligating the double-stranded adaptors formed in step (b) to the ends of the double-stranded DNA fragments created in step (a) to form a first plurality of continuous nucleic acid sequences of the double-stranded DNA fragments flanked by adaptors on each end of the DNA fragments, wherein a first portion of the DNA fragments is flanked at each end by adaptors having identical nucleotide sequences and a second portion of the DNA fragments is flanked at each end by adaptors having non-identical nucleotide sequences;

(d) quantifying the amount of DNA fragments resulting from step (c) of different lengths as a function of their location in the genome from which the DNA specimen was derived;

(e) digesting a second sample of the DNA specimen using the methylation-insensitive isoschizomer of the methylation-sensitive restriction enzyme to create double-stranded DNA fragments of ≤50 bp up to 2000 bp representing the total potential repertoire of DNA fragments that would be created by the methylation-sensitive restriction enzyme in the absence of cytosine methylation at that restriction enzyme target site in the DNA specimen;

(f) ligating double-stranded adaptors as formed in step (b) to the ends of the double-stranded DNA fragments created in step (e) to form a second plurality of continuous nucleic acid sequences of the double-stranded DNA fragments flanked by adaptors on each end of the DNA fragments, wherein a first portion of the DNA fragments is flanked at each end by adaptors having identical nucleotide sequences and a second portion of the DNA fragments is flanked at each end by adaptors having non-identical nucleotide sequences;

(g) quantifying the amount of DNA fragments resulting from step (0 of different lengths as a function of their location in the genome from which the DNA specimen was derived, wherein the steps of quantifying the amounts of DNA fragments are carried out using polymerase chain reaction (PCR) amplification, wherein PCR amplification is carried out using a $Mg^{2+}$ concentration of 1-3 mM, (h) comparing the amount of the DNA fragments quantified in step (d) with the amount of DNA fragments quantified in step (g) so as to determine the pattern of cytosine methylation at target sites of the restriction enzymes in the DNA specimen, as a function of their location in the genome from which the DNA specimen was derived, wherein a greater amount of DNA fragments quantified in step (d) relative to step (g) indicates less cytosine methylation of the DNA fragments quantified in step (d).

2. The method of claim 1, wherein the methylation-sensitive restriction enzyme and the methylation-insensitive isoschizomer of the methylation-sensitive restriction enzyme are selected from the group consisting of: the methylation-sensitive restriction enzyme is HpaII and the methylation-insensitive isoschizomer is MspI, the methylation-sensitive restriction enzyme is AgeI and the methylation-insensitive isoschizomer is CspAI, the methylation-sensitive restriction enzyme is AdeI and the methylation-insensitive isoschizomer is DraIII, the methylation-sensitive restriction enzyme is SmaI and the methylation-insensitive isoschizomer is XmaI, the methylation-sensitive restriction enzyme is MbiI and the methylation-insensitive isoschizomer is BsrBI, the methylation-sensitive restriction enzyme is AvaI and the methylation-insensitive isoschizomer is BsoBI, the methylation-sensitive restriction enzyme is PdmI and the methylation-insensitive isoschizomer is XmnI, the methylation-sensitive restriction enzyme is AatII and the methylation-insensitive isoschizomer is ZraI, the methylation-sensitive restriction enzyme is Ecl136II and the methylation-insensitive isoschizomer is SacI, the methylation-sensitive restriction enzyme is PleI and the methylation-insensitive isoschizomer is MlyI, the methylation-sensitive restriction enzyme is DpnI and the methylation-insensitive isoschizomer is CfuI, the methylation-sensitive restriction enzyme is PfeI and the methylation-insensitive isoschizomer is TfiI, the methylation-sensitive restriction enzyme is SalI and the methylation-insensitive isoschizomer is BsoFI, the methylation-sensitive restriction enzyme is Fnu4HI and the methylation-insensitive isoschizomer is BsoFI, the methylation-sensitive restriction enzyme is HpyF10VI and the methylation-insensitive isoschizomer is MwoI, the methylation-sensitive restriction enzyme is NheI and the methylation-insensitive isoschizomer is BmtI, the methylation-sensitive restriction enzyme is NgoPII and the methylation-insensitive isoschizomer is HaeIII, the methylation-sensitive restriction enzyme is SfoI and the methylation-insensitive isoschizomer is NarI, the methylation-sensitive restriction enzyme is BsmFI and the methylation-insensitive isoschizomer is FaqI, the methylation-sensitive restriction enzyme is NlaIV and the methylation-insensitive isoschizomer is BspLI, the methylation-sensitive restriction enzyme is Asp718I and the methylation-insensitive isoschizomer is KpnI, the methylation-sensitive restriction enzyme is Eco47I and the methylation-insensitive isoschizomer is AflI, the methylation-sensitive restriction enzyme is AhaII and the methylation-insensitive isoschizomer is BsaHI, the methylation-sensitive restriction enzyme is RsaI and the methylation-insensitive isoschizomer is Csp6I, the methylation-sensitive restriction enzyme is BsmAI and the methylation-insensitive isoschizomer is Alw26I, the methylation-sensitive restriction enzyme is Alw26I and the methylation-insensitive isoschizomer is BsmAI, the methylation-sensitive restriction enzyme is PmeI and the methylation-insensitive isoschizomer is MssI, the methylation-sensitive restriction enzyme is BsrFI and the methylation-insensitive isoschizomer is BssAI, the methylation-sensitive restriction enzyme is MroI and the methylation-insensitive isoschizomer is AccIII, and the methylation-sensitive restriction enzyme is NspV and the methylation-insensitive isoschizomer is SfuI.

3. The method of claim 1, wherein the methylation-sensitive restriction enzyme is HpaII and the methylation-insensitive isoschizomer of the methylation-sensitive restriction enzyme is MspI.

4. The method of claim 1, which comprises:
annealing a first pair of oligonucleotides to each other to form a first adaptor; and
annealing a second pair of oligonucleotides to each other to form a second adaptor, wherein the second pair of oligonucleotides has a different nucleotide sequence than the first pair of oligonucleotides.

5. The method of claim 4, wherein the first pair of oligonucleotides and the second pair of oligonucleotides are present in equal amounts.

6. The method of claim 1, which comprises:
annealing a first pair of oligonucleotides to each other to form a first adaptor;
annealing a second pair of oligonucleotides to each other to form a second adaptor, wherein the second pair of oligonucleotides has a different nucleotide sequence than the first pair of oligonucleotides; and
annealing a third pair of oligonucleotides to each other to form a third adaptor, wherein the third pair of oligonucleotides has a different nucleotide sequence than the first and second pairs of oligonucleotides.

7. The method of claim 6, wherein the first pair of oligonucleotides, the second pair of oligonucleotides and the third pair of oligonucleotides are present in equal amounts.

8. The method of claim 1, wherein the oligonucleotides are at least 10 nucleotides in length.

9. The method of claim 1, wherein at least one of the oligonucleotides is at least 10 nucleotides.

10. The method of claim 1, wherein formation of a continuous nucleic acid sequence of a DNA fragment flanked on each end by adaptors having non-identical nucleotide sequences prevents folding of the DNA fragment back upon itself and annealing between complementary adaptor sequences.

11. The method of claim 10, wherein the DNA fragment is less than 200basepairs in length.

12. The method of claim 1, wherein the use of a plurality of different adaptors increases the number of loci that are examined in the DNA sample by at least 50% over the number of loci that can be examined using a single type of adaptor.

13. The method of claim 1, which further comprises annealing the adaptors formed to the ends of the DNA fragments prior to the ligation performed in steps (c) and (f).

14. The method of claim 1, wherein the double-stranded DNA fragments created in steps (a) and (e) have at both ends of the fragments one strand of DNA that is longer than the other strand thereby creating an overhanging end on each end of the DNA fragments.

15. The method of claim 1, wherein the double-stranded adaptors have an end that is complementary to the nucleotide sequence of the ends of the DNA fragments created by restriction enzyme digestion.

16. The method of claim 1, wherein the double-stranded DNA fragments created in steps (a) and (e) have blunt ends without overhangs.

17. The method of claim 1, wherein the steps of quantifying the amounts of DNA fragments are carried out using LM-polymerase chain reaction (ligation mediated-PCR) amplification and microarray analysis.

18. The method of claim 17, wherein PCR amplification selectively amplifies DNA fragments less than 2000 basepairs in length.

19. The method of claim 1, wherein PCR amplification is carried out using a $Mg^{2+}$ concentration of 2 mM.

20. The method of claim 17, wherein PCR amplification is carried out using betaine to improve melting of DNA.

21. The method of claim 20, wherein betaine is used at a 1 molar concentration.

22. The method of claim 17, which further comprises hybridizing probes to the DNA fragments to a microarray of oligonucleotides representing specific loci of the DNA specimen.

23. The method of claim 22, wherein the loci are located at regions of DNA that are rich in restriction enzyme recognition sites.

24. The method of claim 22, wherein the loci are located at gene promoter sites.

25. The method of claim 1, wherein the steps of quantifying the amounts of DNA fragments are carried out using DNA sequencing.

26. The method of claim 1, wherein the DNA specimen is genomic DNA.

27. The method of claim 1, wherein the DNA specimen is from a specific tissue.

28. The method of claim 27, wherein the tissue is selected from the group consisting of skeletal muscle, cardiac muscle, smooth muscle, kidney, bladder, lung, liver, brain, pancreas, spleen, eye, skin, bone, hair, breast, ovary, prostate, esophagus, stomach, intestines, colon, rectum, glia, central nervous system tissue, and peripheral nervous system tissue.

29. The method of claim 1, wherein the DNA specimen is obtained from blood, urine, stool, sputum or saliva.

30. The method of claim 1, wherein the DNA specimen is obtained from a subject having a disease or a subject suspected of having a disease.

31. The method of claim 30, wherein the disease is a cancer or a developmental disease.

* * * * *

UNITED STATES PATENT AND TRADEMARK OFFICE
CERTIFICATE OF CORRECTION

| | | |
|---|---|---|
| PATENT NO. | : 8,642,294 B2 | Page 1 of 1 |
| APPLICATION NO. | : 12/451431 | |
| DATED | : February 4, 2014 | |
| INVENTOR(S) | : John M. Greally and Eli Hatchwell | |

It is certified that error appears in the above-identified patent and that said Letters Patent is hereby corrected as shown below:

Column 1, lines 15-20, should read:

-- STATEMENT OF GOVERNMENT SUPPORT

This invention was made with government support under grant number CA111577 awarded by the National Institutes of Health. The government has certain rights in the invention. --

Signed and Sealed this
Twenty-ninth Day of December, 2015

Michelle K. Lee
*Director of the United States Patent and Trademark Office*